US006335173B1

(12) United States Patent
Kaplan

(10) Patent No.: US 6,335,173 B1
(45) Date of Patent: Jan. 1, 2002

(54) METHODS FOR DETECTING AN ANALYTE OF INTEREST USING TYRAMIDE COATING TECHNOLOGY

(75) Inventor: David R. Kaplan, Shaker Heights, OH (US)

(73) Assignee: Verve, Ltd. c/o James Bell, Pepper Pike, OH (US)

(*) Notice: Subject to any disclaimer, the term of this patent is extended or adjusted under 35 U.S.C. 154(b) by 0 days.

(21) Appl. No.: 09/229,001

(22) Filed: Jan. 12, 1999

(51) Int. Cl.[7] ........................ G01N 33/53; G01N 33/567
(52) U.S. Cl. ............................. 435/7.2; 435/2; 435/4; 435/7.2; 435/7.23; 435/7.24; 435/7.72; 435/7.9; 435/40.51; 435/40.52; 435/172; 436/546; 436/63; 436/64; 436/800; 436/805; 436/808; 436/813
(58) Field of Search .......................... 435/2, 4, 6, 7.2, 435/7.9, 7.21, 7.23, 7.24, 7.32, 40.5, 7.72, 40.51, 40.52, 172; 436/63, 64, 537, 545, 546, 800, 805, 808, 813, 825

(56) References Cited

U.S. PATENT DOCUMENTS

| 5,196,306 A | 3/1993 | Bobrow et al. ............... 435/7.9 |
| 5,583,001 A | 12/1996 | Bobrow et al. ............... 435/7.5 |
| 5,731,158 A | 3/1998 | Bobrow et al. ............... 435/7.5 |

FOREIGN PATENT DOCUMENTS

WO 98/01757 1/1998

OTHER PUBLICATIONS

Mayer et al., Biotinyl–Tyramide: A Novel Approach for Electron Microscopic Immunocytochemistry, The Journal of Histochemistry and Cytochemistry 45(11): 1449–1454, May 1997.*

Schonhuber et al., Improved Sensitivity of Whole Cell Hybridization by the Combination of Horse–Radish Peroxidase–Labeled Oligonucleotides and Tyramide Signal Amplification, Applied and Environmental Microbiology, 63(8): 3268–3273, Aug. 1997.*

Wasielowski et al., Tyramine Amplification Technique in Routine Immunohistochemistry, The Journal of Histochemistry and Cytochemistry 45(11): 1455–1459, May 1997.*

Raikow, Enhancement if CD4, CD5, CD8, and Bcl–2 immunohistochemical staining with biotinyl–tyramide, Journal of Histotechnology, 21(3): 237–239, Sep. 1998.*

Earnshaw et al., "Signal amplification in flow cytometry using biotin tyramine," Cytometry 35:176–179 (1999).

Bobrow et al., "Catalyzed Reporter Deposition, A Novel Method of Signal Amplification: Application to Immunoassays," *Journal of Immunological Methods* 125:279–285 (1989).

Bobrow, "Catalyzed Reporter Deposition, A Novel Method of Signal Amplification: II. Application to Membrane Immunoassays," *Journal of Immunological Methods* 137:103–112 (1991).

(List continued on next page.)

*Primary Examiner*—Long V. Le
*Assistant Examiner*—Gailene R. Gabel
(74) *Attorney, Agent, or Firm*—Foley & Lardner

(57) ABSTRACT

The present invention relates to methods of tyramide coating live cells for flow cytometry, using catalyzed reporter deposition and serial amplification staining. A catalyzed reporter deposition or an analyte dependent enzyme activation system is described for detecting and/or quantitating an analyte of interest on the surface of a cell by flow cytometry. Also described is a method for serial amplification staining by tyramide coating cells which possess an analyte of interest or a solid phase to which an analyte is bound.

30 Claims, 6 Drawing Sheets

OTHER PUBLICATIONS

Chao et al., "Immunofluorescence Signal Amplification By the Enzyme–Catalyzed Deposition of a Fluorescent Reporter Substrate (CARD)," *Cytometry* 23:48–53 (1996).

Classon, et al., "Thymic–Shared Antigen–1 (TSA–1) A Lymphostromal Cell Membrane Ly–6 Superfamily Molecule with a Putative Role in Cellular Adhesion," *Dev. Immunol.* 6(1–2):149–156 (1998).

Hopman, Anton, et al., "Rapid Synthesis of Biotin–, Digoxigenin–, Trinitrophenyl–, and Florochrome–labeled Tyramides and Their Application for In Situ Hybridization Using CARD Amplification," *Journal of Histochemistry and Cytochemistry* 46(6):771–777 (1998).

Kato et al., "Differential Expression of the Murine Ly–6A/E Antigen Homolog of Human Squamous Cell Carcinoma Antigen E48 During Malignant Transformation and Tumor Progression of Squamous Cell Carcinoma Line Pam 212," *Otolaryngol Head Neck Surg.*, 119(4):408–411 (1998).

Kishimoto, et al., Leukocyte Typing VI: White Cell Differentiation Antigens, Garland Publishing, Inc., New York 1997 (Table of Contents).

Koshkin, et al., "Novel Convenient Syntheses of LNA [2.2.1] Bicyclo Nucleosides," *Tetrahedron Letters* 39:4381–4384 (1998).

Lollini et al., "Flow Cytometry on Intracellular Antigens After Tyramide Signal Amplification," Immunological Blackboard: Bulletin of the Gruppo Di Cooperazione in Immunologia 1:2 (1998).

Malisius et al., "Constant Detection of CD2, CD3, CD4, and CD5 in Fixed and Paraffin–Embedded Tissue Using the Peroxidase–Mediated Deposition of Biotin–Tyramide," *The Journal of Histochemistry Cytochemistry* 45(12):1665–1672 (1997).

Melamed et al., *Flow Cytometry and Cell Sorting*, $2^{nd}$ ed. Wiley–Liss, New York 1990 (Table of Contents).

Nolan et al., "The Emergence of Flow Cytometry for Sensitive, Real–time Measurements of Molecular Interactions," *Nature Biotechnology* 16 (1998).

Pichert et al., "Selection and Immunomagnetic Purging of Peripheral Blood CD34+ Cells for Autologous Transplantation in B–cell non–Hodgkin's Lymphomas," *Ann. Oncol.* 9:51–54 (1998).

Rowley, et al., "Isolation of CD34+ Cells from Blood Stem Cell Components Using the Baxter Isolex System," *Bone Marrow Transplantation* 21:1253–1262 (1998).

* cited by examiner

METHODS FOR DETECTING AN ANALYTE OF INTEREST USING TYRAMIDE COATING TECHNOLOGY

The present invention relates to methods of using tyramide coated live cells for flow cytometry, preferably using catalyzed reporter deposition and amplification staining.

BACKGROUND OF THE INVENTION

The following information is presented solely to assist the understanding of the reader, and none of the information is admitted to describe or constitute prior art to the claims of the present invention.

Flow cytometry is a sensitive and quantitative method for measuring the fluorescence or light scatter of particles or cells. This method has been widely used to study cellular physiology, especially as it relates to the immune system and control of the cell cycle. Nolan et al, "The Emergence of Flow Cytometry for Sensitive, Real-time Measurements of Molecular Interactions", *Nature Biotechnology,* Vol. 16, (1998), which is incorporated by reference herein in its entirety including any drawings, describe recent flow cytometry developments for fields as diverse as ligand binding and enzyme kinetics, drug screening, diagnostics and detection of soluble agents, and DNA sequence detection or analysis. They describe developments such as advances in automated sample handling, molecular approaches for incorporating affinity tags or fluorescent probes into proteins and the availability of microsphere reagents that enable multiplexing.

Flow cytometric analysis of cell surface molecules is a technology used in both medical diagnostic laboratories and biomedical research laboratories. In clinical practice flow cytometry is used for samples derived from patients infected with human immunodeficiency virus type 1, patients with leukemias and lymphomas, and patients with primary immunodeficiences.

Lollini et al., "Flow Cytometry on Intracellular Antigens After Tyramide Signal Amplification", Immunological Blackboard: *Bulletin of the Gruppo Di Cooperazione in Immunologia,* Vol. 1, Number 2 (1998), which is incorporated herein by reference in its totality, including any drawings, describes tyramide signal amplification (TSA) for detection of intracellular antigens by flow cytometry and indicates that TSA is not superior to conventional techniques for detecting surface antigens on live cells. Lollini et al. states on page 5, "(t)he main problem appeared to be a high level of spontaneous activation and non-specific binding of the fluorescent substrate to live cell membranes".

Various methods have been described for assaying biological samples with amplified reporter systems. Bobrow et al., U.S. Pat. Nos. 5,196,306, 5,583,001 and 5,731,158, which are all herein incorporated by reference in their totality including any drawings, describe methods for detecting or quantitating analytes using an analyte dependent enzyme activation system as well as catalyzed reporter deposition methods. Specifically, Bobrow et al. describe calorimetric and fluorometric solid phase enzyme immunoassays which are enhanced by amplification of the reporter molecules.

Chao et al., "Immunofluorescence Signal Amplification By The Enzyme-Catalyzed Deposition Of A Fluorescent Reporter Substrate (CARD)", *Cytometry* 23:48–53 (1996), describe a CARD system that uses horseradish peroxidase substrate Cy3.29-tyramide to deposit fluorogen molecules onto fixed tissues and cells as well as proteins bound to nitrocellulose membranes, with up to a 15 fold increase over standard indirect immunofluorescence methods.

Malisius et al., "Constant Detection of CD2, CD3, CD4, And CD5 In Fixed and Paraffin-Embedded Tissue Using The Peroxidase-Mediated Deposition Of Biotin-Tyramide", *The Journal of Histochemistry and Cytochemistry,* Vol. 45(12) :1665–1672, (1997), describe a method for enhancing detection of leukocyte antigens in formalin-fixed tissue samples.

SUMMARY OF THE INVENTION

This invention features methods for enhancing the detection and/or quantitation of an analyte of interest on a live cell in flow cytometric analysis. The invention provides a method for tyramide coating live cells for flow cytometry, wherein live cells are preferably exposed to a catalyzed reporter deposition system which results in specific tyramide coating of cells which contain or express an analyte of interest. The invention, however, features flow cytometric detection of tyramide coated live cells regardless of how the cell is coated with tyramide and encompasses the use of any such cells which can be prepared using various techniques known by those skilled in the art. Thus, the present invention allows for increased detection of an analyte of interest in a sample of live cells by flow cytometric methods. Furthermore, the present invention allows for detection of analytes which are present in low copy number in a live cell sample.

The term "low copy number" means that the analyte of interest is present on or in the cell but is not represented in an easily detectable amount. An aspect of the present invention is that rare, hard to detect analytes may be readily detected by the increase in the staining of the cell caused by the amplification of the labeling molecule. Hence, a low copy number analyte, such as the Fas ligand, would not have to be over-expressed in order to be detected by flow cytometry. The low copy number is preferably less than 20,000 molecules/cellular surface, more preferably less than 10,000 molecules/cellular surface and most preferably less than 5000 molecules/cellular surface.

In a first aspect, the present invention features a method of flow cytometry which involves coating live cells with tyramide and analyzing the cells with a flow cytometric device.

By "tyramide coating" or "coating live cells with tyramide" is meant to relate to any process which results in cell surfaces being coated with tyramide, such as the enzyme dependent deposition of tyramide on the surface of cells containing the analyte of interest. In the presence of oxygen radicals, short lived tyramide radicals are formed which form covalent linkages with aromatic molecules such as certain amino acids (tyrosine and tryptophan for example) found in most proteins. Since cell surfaces have an abundance of proteins the tyramide radicals bind to the surface of the cell to which it is in closest proximity. The generation of oxygen radicals, by the catalytic activity of the enzymatic portion of the second binding partner and the appropriate substrate, over a period of time, produces tyramide radicals that coat the surface of the cell. The live cells preferably are not fixed before contacting with the binding partner specific for the analyte of interest, and have not been treated with a conventional fixation procedure such as methanol fixation. See, Lollini et al., supra, page 2. However the cells may be fixed by procedures known in the art after contacting with the binding partner which is specific for the analyte of interest.

What is meant by "live cells" is that the cells to be assayed for an analyte of interest are viable when contacted with the binding partner for the analyte of interest. In certain embodiments the cells are viable during flow cytometric analysis. The cells are preferably viable during and after flow cytometric analysis to allow for selection and/or sorting of cells which have or do not have the analyte of interest, if desired, and used for therapeutic and/or research methods. It is known by those of skill in the art that the cells may also be manipulated to remain in a certain stage of the cell cycle during analysis. It is also understood that the cells may be fixed for analysis after contact with the binding partner specific for the analyte of interest.

By "viable" is meant that the cells are capable of being grown, cultured, or further propagated at the time at which contact with the binding partner for the analyte of interest occurs. Essentially, viable cells are alive and capable of mitotic or meiotic division and further growth after contact with the binding partner specific for the analyte of interest. In a preferred embodiment of the invention, the cells are capable of being grown, cultured, or further propagated after being analyzed by flow cytometry.

By "cells" is meant the smallest unit of living structure capable of either aided or un-aided existence, composed of a membrane-enclosed interior which may contain a nucleus or nucleoid, free compact DNA, and/or other organelles such as mitochondria, the golgi apparatus, centrioles, endoplasmic reticulum, vacuoles, microsomes, lysosomes, ribosomes and the like. The cells can be bacterial cells as well as eukaryotic cells such as plant cells, yeast or fungal cells or mammalian cells. In a preferred embodiment, the live cells are mammalian cells. Examples of various cells available for flow cytometric analysis exist throughout the art. Cell types can include but are not limited to basal, epithelial, erythrocytes, platelets, lymphocyte, T-cells, B-cells, natural killer cells, granulocytes, monocytes, mast cells, Jurkat, neurocyte, neuroblast, cytomegalic, dendritic, macrophage, blastomere, endothelial, HeLa, tumor, interstitial, Kupffer, Langerhans', Langhans, littoral, tissue cells such as muscle cells, adipose cells, CHO cells, KFL9, K562, enucleated cells and the like as well as cells readily prepared and sold by immunological and microbiological resources currently.

By "aided existence" is meant adding components to the buffer or medium containing the cells which allows the cell to remain viable.

In a preferred embodiment, the present invention features a method for tyramide coating live cells for flow cytometric analysis by contacting the live cells with one or more of the following; a first binding partner specific for the analyte of interest, a second binding partner with enzymatic activity and which specifically binds to the first binding partner, a substrate for the enzymatic activity of the second binding partner, and a labeling molecule containing tyramide. The tyramide containing labeling molecule is coated on the cells possessing the analyte of interest as a result of the product of the enzymatic activity of the second binding partner and the substrate reacting with the tyramide. A detectable marker may be added after tyramide coating to facilitate flow cytometric analysis. The detectable marker can be a fluorochrome molecule which is attached to a binding partner specific for the tyramide containing molecule. In a preferred embodiment the labeling molecule is tyramide attached to a fluorochrome. In a further embodiment, the tyramide containing molecule is comprised of tyramide attached to a fluorochrome and a binding partner specific for the binding partner which is bound to the analyte of interest.

The term "binding partner" refers to biochemical or chemical molecules such as polypeptides, glycoproteins, glycolipids, lipids, or nucleic acids which bind to the analyte of interest or to a first binding partner which specifically binds to the analyte of interest. Binding partners may be attached naturally through contacting a molecule with a receptor for such a molecule. The polypeptides can be conjugated proteins, antibodies and the like. Hence, a binding partner may consist of an antibody bound to a label or an enzyme bound to a binding partner, or an antibody bound to a binding partner. Pairs of binding partners can be but are not limited to, (i) streptavidin and biotin, (ii) an antibody and an epitope, (iii) an antibody and a protein, (iv) a protein and a receptor molecule or receptor protein, (v) a nucleic acid and a nucleic acid, (vi) a nucleic acid and a protein, (vii) a hormone and a hormone receptor, (viii) a cytokine and a cytokine receptor. The nucleic acids can be DNA, RNA, mixed oligonucleotides, peptide nucleic acids (PNA), Locked Nucleic Acids (LNA) as described in Koshkin, et al., Tetrahedron Letters 1998 39:4381–4384, which is incorporated herein by reference in its entirety including any drawings, and the like. In a preferred embodiment the binding partner with specificity to a first binding partner which has bound the cellular analyte of interest, has enzymatic activity. It would be clear to one of skill in the art that various combinations of binding partners which are capable of binding by either covalent or non-covalent means can be used in the invention to tyramide coat live cells.

By "contacting" is meant bringing the live cells into close proximity with the binding partners in a manner which allows the cellular analytes of interest to interact with and bind to binding partner. "Contacting" preferably refers to bringing the live cells into close proximity with the binding partners in a manner which allows previously bound partners to interact with unbound partners and thereby bind. "Contacting" may also refer to bringing the live cells into close proximity with an enzyme substrate in a manner which allows any previously bound partners which posses enzymatic activity to interact with the substrate for the enzyme.

By "analyte of interest" is meant a molecule in or on the surface of a cell. The molecule can be a protein, glycoprotein, glycolipid, lipid, a nucleic acid, or a biochemical or chemical molecule as defined above. In preferred embodiments the molecule is a cell surface expressed molecule such as but not limited to cell surface ligands such as Fas ligand (which binds CD95) and the ligands for CD1 through CD166, CD1 through CD166 as disclosed in "Leukocyte Typing VI: White Cell Differentiation Antigens" Edited by Kishimoto et al., Garland Publishing, Inc. New York 1997, which is incorporated herein by reference in its entirety including any drawings, hormone receptor molecules, cytokine receptor molecules, MHC class I, MHC class II, cell receptors for IgG, and IgE, cell receptors for complement components such as receptors for C3a, C5a, CR1 and CR3, T-Cell or B-Cell receptor molecules, viral antigens, tumor antigens, histocompatibility antigens, differentiation antigens, T-cell antigen, Ly antigen, Ly-6 (Classon et al., Dev. Immunol. Vol. 6(1–2):149–156, 1998, Kato et al., *Otolaryngol Head Neck Surg.* Vol. 119(4): 408–411, 1998, IgD, IgM and the like. Also included are cell surface molecules within families of molecules such as those disclosed above.

In another embodiment, the cell is transformed to express a surface molecule that is not a natural component of the cell. These transformed cells may express molecules such as bacterial antigens, viral proteins or cellular proteins normally expressed intra-cellularly and engineered for secretion and expression on the surface of the cell. This type of transformation is common and routinely preformed by those in the art and generally involves the insertion of exogenous DNA or RNA constructs composed of a sequence specific for the molecule of interest wherein the construct is configured and arranged in a manner suitable for expression when inside of the cell. In addition the analyte of interest can be a molecule which has been inserted into the cell by experimental methods. This molecule may be a dye or a chemical molecule which the cell can internalize or bind on it's surface.

The term "enzymatic activity" refers to the ability of the binding partner to act as a catalyst to induce chemical changes in other substances. In one embodiment the enzymatic activity catalyzes the dehydrogenation (oxidation) of various substances in the presence of hydrogen peroxide. In a preferred embodiment the enzymatic activity refers to the reaction between the horseradish peroxidase portion of a binding partner and a peroxide substrate. The enzymatic activity could also be the result of the reaction between enzymes such as, but not limited to, oxidases, phosphatases, esterases and glycosidases and their respective substrates. By "labeling molecule" is meant that substance which ultimately binds to the cell or binding partner attached to the cell that leads to the deposition/coating of tyramide on the surface of the cell. The labeling molecule can be tyramide alone or tyramide conjugated to a binding partner for either the analyte of interest or a first binding partner, or tyramide conjugated with a binding partner and a fluorochrome. In one embodiment the labeling molecule comprises a phenol group and is capable of being conjugated with a molecule such as biotin, a fluorochrome or a binding partner. In a preferred embodiment the labeling molecule is tyramide conjugated with biotin. The labeling molecule generally brings tyramide into close proximity with the cell. Once bound to the cell the biotin-tyramide conjugate is available for binding to a detectable marker such as a streptavidin-fluorochrome conjugate.

By "detectable marker" is meant that substance or molecule which is attached to the binding partner or added to tyramide labeled cells, and which can be detected by flow cytometric analysis. Such markers are generally fluorochromes and include but are not limited to fluorescein, phycoerythrin, CY5, allophycocyanine, Texas Red, peridenin chlorophyll, cyanine, tandem conjugates such as phycoerythrin-CY5, and the like.

In preferred embodiments of the invention the method for tyramide coating live cells for flow cytometric analysis results in increased detection by flow cytometry. The increase is preferably 4 to 5 fold in fluorescent signal with respect to standard flow cytometry, more preferably 40 to 65 fold, most preferably at least 50 fold and up to 61 fold greater with respect to standard flow cytometric measurements.

By "standard flow cytometry" is meant analysis of cell samples by commercially available devices such as those provided by Becton-Dickenson or Beckman-Coulter for flow cytometric analysis of cell samples or such other devices currently known or which can be produced based on currently available technology. Standard flow cytometry can encompass multiparametric DNA analysis, platelet studies, reticulocyte enumeration, cell biology/functional studies, innovative research in immunobiology, cell physiology, molecular biology, genetics, microbiology, water quality and plant cell analysis as well as a broad range of research applications. Current flow cytometers are manufactured with the ability to measure more than one and up to four separate fluorochrome colors. Under standard methods for flow cytometric analysis a specific labeled antibody is added to live cells expressing a given analyte. The antibody is labeled with the appropriate fluorochrome which allows for detection. The analysis may involve quantitation and/or detection of the analyte and may involve sorting or harvesting the cells possessing the analyte of interest.

In an additional embodiment of the invention the binding partner which is specific for the analyte of interest is chemically attached to biotin, or biotinylated by methods which are routine and well known in the art. In another embodiment the binding partner is a biotinylated antibody. In a further embodiment the binding partner which is specific for the analyte of interest is a biotinylated construct combining a protein or nucleic acid molecule with biotin. Linking the respective binding partners to the biotin molecule prepares the binding partner to be readily available to binding partners which have been chemically attached to the glycoprotein streptavidin which has high affinity for binding the biotin molecule. Those in the art would readily recognize that other proteins which specifically bind molecules with similar characteristics as biotin and streptavidin and which are readily attached to antibodies or cellular analytes are within the scope of the present invention.

In another embodiment of the invention the binding partner which possesses enzymatic activity is a streptavidin-enzyme conjugate. Streptavidin is a 60,000 Dalton extracellular protein of Streptomyces avidinii with four high-affinity biotin binding sites. Analogues of Streptavidin or recombinant proteins of Streptavidin are within the scope of the present invention. Streptavidin is readily conjugated with other proteins and such conjugates can be but are not limited to streptavidin-peroxidase, streptavidin-hydrolase, streptavidin-oxidase, streptavidin-glycosidase and streptavidin-phosphatase. In a preferred embodiment the streptavidin-enzyme conjugate is streptavidin-horseradish peroxidase. The binding partner which possesses enzymatic activity is also called the enzyme in different embodiments of the invention.

An additional embodiment of the present invention features a method for tyramide coating live cells for multiparameter flow cytometric analysis by contacting the live cells with the following; a first binding partner specific for a first analyte of interest, a second binding partner with enzymatic activity and which specifically binds to the first binding partner, a substrate for the enzymatic activity of the second binding partner, and a labeling molecule containing tyramide. After tyramide coating and the addition of a detectable marker, the live cells are contacted with a third binding partner specific for a second analyte of interest, a fourth binding partner with enzymatic activity and which specifically binds to the third binding partner, a substrate for the enzymatic activity of the fourth binding partner, and a labeling molecule containing tyramide and specific for the third or fourth binding partners. The tyramide containing labeling molecules are coated on the cells possessing the analytes of interest as a result of the enzymatic activities of the second and fourth binding partners causing tyramide deposition. Detectable markers are added after tyramide coating to facilitate flow cytometric analysis. The first and second detectable markers can be the same fluorochrome molecule which is attached to a binding partner specific for the tyramide containing molecules and would be detected by an increase in fluorescence with respect to single fluorochrome bound cells. In another embodiment the first and second detectable markers are different fluorochrome molecules which are selected based on the wavelength at which they fluoresce. The flow cytometric analysis would comprise analyzing the cells at the various wavelengths to determine the presence or absence of both bound fluorochromes.

By "multiparameter flow cytometric analysis" is meant detecting more than one analyte of interest in a sample of cells, or on cells within a population of heterogeneous cells at a given time by flow cytometry.

It is readily recognizable that more than 2 fluorochromes may be selected for the preceding embodiment and the restriction to 4 fluorochromes is presently based on available flow cytometric devices. Hence, at the present up to 4 different molecules may be analyzed by flow cytometric methods. However, within the scope of the invention, any improvements to such devices which allow for additional wavelengths or fluorochromes to be distinguished and therefore it would be reasonable to select additional fluorochromes to detect more than 4 analytes.

In another embodiment the present invention provides a method for tyramide coating live cells for double label analysis for flow cytometry by contacting the live cells with the following; a first binding partner specific for a first analyte of interest, a second binding partner with enzymatic activity and which specifically binds to the first binding partner, a substrate for the enzymatic activity of the second binding partner, and a labeling molecule containing tyramide. In one embodiment of the present invention, after tyramide coating and the addition of a detectable marker, the live cells are contacted with a third binding partner specific for a second analyte of interest. The third binding partner is preferably conjugated to a detectable marker. In a further embodiment, the third binding partner is added with the addition of the first binding partner. In an even further embodiment of the present invention, the third binding partner is added at anytime during double label analysis as this third binding partner, which is preferably conjugated to a detectable marker, is not directly associated with the amplification of tyramide coating associated with the first and second binding partners.

By "double label" is meant labeling the live cells by tyramide coating for flow cytometry and further labeling the live cells by standard flow cytometric methods.

In another embodiment the present invention provides a method for tyramide coating live cells for flow cytometry using serial amplification by contacting the live cells with the following; a first binding partner specific for a first analyte of interest, a second binding partner with enzymatic activity and which specifically binds to the first binding partner, a substrate for the enzymatic activity of the second binding partner, and a labeling molecule containing tyramide which is attached to and/or contains a binding partner which enables the conjugated tyramide-binding partner labeling molecule to bind to the second binding partner with enzymatic activity. After this initial tyramide coating, the cells are further contacted with additional second binding partner, additional substrate for said second binding partner, and additional labeling molecule containing tyramide. The sequential addition of both the labeling molecule (i.e. tyramide or another detectably labeled phenol attached to biotin) that can bind to the second binding partner with enzymatic activity and the second binding partner, can be repeated as many times as necessary to achieve the desired level of deposited labeling molecule, detectable label, or signal. This novel procedure results in the amplification of labeling molecules deposited on the cell surface. After the desired number of amplifications or sequential additions, the presence of the labeling molecule containing tyramide is detected by the addition of a detectable marker which binds to the labeling molecule, and, is capable of either directly or indirectly generating a signal. This novel process can be repeated as many times as necessary and results in further tyramide coating of the live cells and an enhanced detection of low copy number analytes.

By "serial amplification" is meant contacting the live cells or an analyte of interest which is bound to a solid phase with repeated coatings of tyramide by additionally contacting the cells with labeling molecules and enzyme-substrate binding pairs.

Hence, an additional aspect of the present invention provides a method for detecting an analyte of interest which is bound to a solid phase by tyramide coating using a serial amplification procedure, by contacting the bound analyte with the following; a first binding partner specific for the analyte of interest, a second binding partner with enzymatic activity and which specifically binds to the first binding partner, a substrate for the enzymatic activity of the second binding partner, and a labeling molecule containing tyramide which is attached to and/or contains a binding partner which enables the conjugated tyramide-binding partner labeling molecule to bind to the second binding partner with enzymatic activity. After this initial tyramide coating, the analyte is further contacted with additional second binding partner, additional substrate for said second binding partner, and additional labeling molecule containing tyramide.

The sequential addition of the labeling molecule (i.e. tyramide or another detectably labeled phenol attached to bioting) that can bind to the second binding partner with enzymatic activity and the second binding partner can be repeated as many times as necessary to achieve the desired level of deposited labeling molecule, detectable label, or signal. This novel procedure results in the serial amplification of labeling molecules deposited on the solid phase. After the desired number of serial amplifications or sequential additions, the presence of the labeling molecule containing tyramide is detected by the addition of a detectable marker which binds to the labeling molecule and is capable of either directly or indirectly generating a signal. This novel process can be repeated as many times as necessary and results in further tyramide coating of the solid phase and enhanced detection of low copy number analytes.

By "solid phase" is meant supports as used in assays, which are well known by those of skill in the art, which include but are not limited to synthetic polymer supports, such as polystyrene, polypropylene, substituted polystyrene, e.g., laminated or carboxylated polystyrene; polyacrylamides; polyamides; polyvinylchloride, and the like; glass beads; agarose; nitrocellulose; nylon; polyvinylidenedifluoride; surface-modified nylon and the like. Preferably the solid phase is chosen or configured so that it contains an excess of proteins that do not bind to the binding partner which is specific for the analyte of interest.

In another embodiment the present invention provides a diagnostic method for tyramide coating live cells for flow cytometry by removing cells from a patient and contacting the cells with the following, a first binding partner specific for the analyte of interest, a second binding partner with enzymatic activity and which specifically binds to the first binding partner, a substrate for the enzymatic activity of the second binding partner, and a labeling molecule containing tyramide, and a detectable marker.

By "diagnostic method" is meant the determination of the nature of a disease. Preferably the disease is caused by a cell, or a changed cell, such as a cancerous cell or a virally infected cell, or a mutated cell, which has a known cell surface analyte. Examples of such methods include but are not limited to determining the phenotype of a lymphoma or leukemia, determining the immunological status of a patient with AIDS or with a primary immunodeficiency syndrome such as severe combined immunodeficiency disease.

In an additional aspect, the present invention provides a method for selecting cells for therapeutic purposes by tyramide coating live cells which possess an analyte of interest, and selecting the live cells for therapeutic purposes.

By "therapeutic purposes" is meant the selection of cells from a sample of heterogeneous cells taken from a patient for use in the treatment of abnormal conditions.

As an example, cells selected by using methods of the invention are useful in patients requiring bone morrow transplantation. Bone marrow transplantation has involved two procedures that utilize the selection of cells based on surface analyte composition for diagnostic and purposes. A first example procedure which involves selection of live cells positive for the cell surface analyte CD34 using antibodies to identify the cells has been used for reconstitution of bone marrow function after marrow ablative chemo-radiotherapy. See Rowley et al., "Isolation of CD34+ cells from blood stem cell components using the Baxter Isolex system" *Bone Marrow Transplantation* Vol. 21:1253–1262 (1998), which is incorporated herein by reference in its entirety including any drawings. The use of tyramide coating for identifying live CD34 positive cells would be advantageous because the technique gives greater separation between positive and negative cells as exemplified by the increase in flow cytometric detection. Furthermore, malignant cells have been purged from bone marrow for autologous transplantation. Purging has used many different technologies including antibody mediated identification of the malignant cells. see Pichert et al., "Selection and Immunogenetic Purging of Peripheral Blood CD34 Positive Cells for Autologous Transplantation in B-cell Non-Hodgkin's Lymphomas" *Ann. Oncol.* Vol. 9:51–54. (1998). For identification of malignant cells in blood or bone marrow using antibodies, the amplification staining procedure would be advantageous because it would give a greater separation between positive and negative subpopulations.

By "patient" is meant an organism which is a donor or recipient of explanted cells or the cells themselves. Preferably, a patient is a mammal or mammalian cells. More preferably, a patient is a human or human cells.

In another embodiment, the present invention provides an antibody-binding partner conjugate configured and arranged for use with methods for tyramide coating live cells for flow cytometry.

In additional embodiment, the present invention provides a device for flow cytometry comprising tyramide coated cells.

In another embodiment, the invention is a method of flow cytometry wherein the improvement comprises coating live cells with tyramide.

In a further embodiment the present invention provides a kit for use with a method of tyramide coating live cells for flow cytometry. The kit includes materials for tyramide coating live cells and/or detecting such cells by flow cytometry. The kit preferably contains components such as, but not limited to, premade buffers, amplification reagents, and a detailed protocol. The premade buffers of the kit of the invention are physiological mediums of a pH which supports the viability of the cells. In one aspect the premade buffers are Ficoll/Hypaque with 0.01% hydrogen peroxide, isotonic buffered saline and 0.005% sodium azide at a pH of between 7.3 and 7.5, and Bovine Serum Albumin at 1%. In further embodiments the kit contains isotonic buffered saline with 0.005% azide at a pH of between 7.3 and 7.5, Ficoll/Hypaque, streptavidin-horseradish peroxidase, peroxide, biotin-tyramide, and detailed protocol.

The amplification reagents include the components of the invention which are responsible for generating tyramide radicals and hence the subsequent coating of the cell which contains or displays the analyte of interest. These amplification reagents can include but are not limited to peroxide, conjugated-peroxidase, tyramide, and conjugated tyramide. In another embodiment of the invention the amplification reagents include a conjugated antibody-enzyme component such as an antibody-horseradish peroxidase conjugate. In yet another embodiment of the invention the kit contains an analyte specific antibody conjugate in it's own buffer which is to be used in the assay. Such an antibody conjugate can be, but is not limited to, an antibody-biotin conjugate or an antibody-horseradish peroxidase conjugate. The antibody may be specific for, but not limited to the following cellular analytes, cell surface ligands such as Fas ligand (which binds CD95) and ligands for CD1 through CD166, surface antigens CD1 through CD166 as disclosed in "Leukocyte Typing VI: White Cell Differentiation Antigens" Edited by Kishimoto et al., Garland Publishing, Inc. New York 1997, supra, hormone receptor molecules, cytokine receptor molecules, MHC class I, MHC class II, viral antigens, tumor antigens, cell receptors for IgG, and IgE, cell receptors for complement components such as receptors for C3a, C5a, CR1 and CR3, T-Cell or B-Cell receptor molecules, T-cell antigen, Ly antigen, Ly-6 (Classon et al., Dev. Immunol. Vol. 6(1–2):149–156, 1998, Kato et al., Otolaryngol Head Neck Surg. Vol. 119(4):408–411, 1998, IgD, IgM and the like. Also included are cell surface molecules within families of molecules such as those disclosed above.

In a further aspect, the invention features a device for serial amplification and/or multiparameter analysis of a sample. Preferably such a device is configured and arranged to repeat the addition of a second binding partner with enzymatic activity and a labeling molecule as described above. One of skill in the art would recognize that a device of this manufacture would be configured to incorporate the addition of a sample believed to possess an analyte of interest, the addition of the binding partners of the method, as described above, and would include instrumentation which incorporates intermediate washing steps which are necessary for immunoassays such as flow cytometry, ELISA, radio-immunoassays, analyte dependent enzyme activation system (ADEAS) assays, catalyzed reporter deposition amplification assays, and the like, or other immunohistochemical staining methods.

Another aspect of the present features a method for detecting or quantitating an analyte in an assay wherein said method comprises using an analyte dependent enzyme activation system, wherein the method is an improvement which comprises repeatedly adding enzyme, substrate and labeling molecule, and wherein repeatedly added labeling molecule is deposited on the cell or a solid phase and can either directly or indirectly generate a signal which can be detected or quantitated.

By "repeatedly added" is meant the enzyme, substrate and labeling molecule are further added after they are initially introduced to the sample. Such an addition can be considered a cycle, where the first addition represents one, or the first, tyramide (detectably labeled phenol) coating event, and subsequent "repeated additions" represent further cycles of tyramide coating. In a preferred embodiment the enzyme, substrate and labeling molecule are repeatedly added more than once. Hence, in a preferred embodiment at least two cycles of tyramide coating are performed.

What is meant by "analyte dependent enzyme activation system" is a labeling method which incorporates a first binding partner specific for an analyte of interest, a second binding partner with enzymatic activity, a substrate for said activity, and a detectably labeled phenol, such as a tyramide-biotin conjugate. The detectably labeled phenol is capable of being activated by the reaction between the enzyme and the substrate in a manner which results in it's being deposited on the surface to which the first binding partner has bound to the analyte of interest. Further examples of analyte dependent enzyme activation systems are discussed in Bobrow et al., U.S. Pat. No. 5,583,001 (1996) and U.S. Pat. No. 5,196,306 (1993), which are herein incorporated by reference in their entirety including any drawings or figures.

The summary of the invention described above is not limiting and other features and advantages of the invention will be apparent from the following detailed description of the invention and from the claims. One of skill in the art would readily recognize that in certain aspects of the invention additional steps may be added, such as washing steps, which are practiced regularly when performing assays which require addition of multiple binding partners or detectable molecules. Such procedures are described herein in the following examples and have been described in the art. Furthermore, the methods described herein have been disclosed, in some instances, in a sequential manner which one of skill in the art would readily recognize as convenient, but not necessary. Hence, in certain aspects of the invention, the binding partners may be added in a sequential manner, simultaneously or in an arbitrary manner which can still result in the binding of an analyte of interest to a binding partner resulting in the tyramide coating of live cells for flow cytometry or the serial amplification of tyramide coating cell surfaces or solid phases for the detection of an analyte of interest.

BRIEF DESCRIPTION OF THE DRAWINGS

The drawings will herein briefly be described.

FIG. 4 shows the flow cytometric results for detecting CD45 on Jurkat cells by tyramide coating cells using a horseradish-anti CD45 antibody conjugate vs. an antibody control conjugate.

FIG. 5 shows the results of experiments to eliminate "bystander staining".

FIG. 6 shows the results of experiments in which peripheral blood mononuclear cells have been treated with phytohemagglutinin and interleukin 2, washed and cultured for 2 days with phorbol myristic acetate and ionomycin.

The drawings are not necessarily to scale, and certain features of the invention may be exaggerated in scale and shown in schematic form in the interest of clarity and conciseness.

DETAILED DESCRIPTION OF THE PREFERRED EMBODIMENTS

Figure 2:
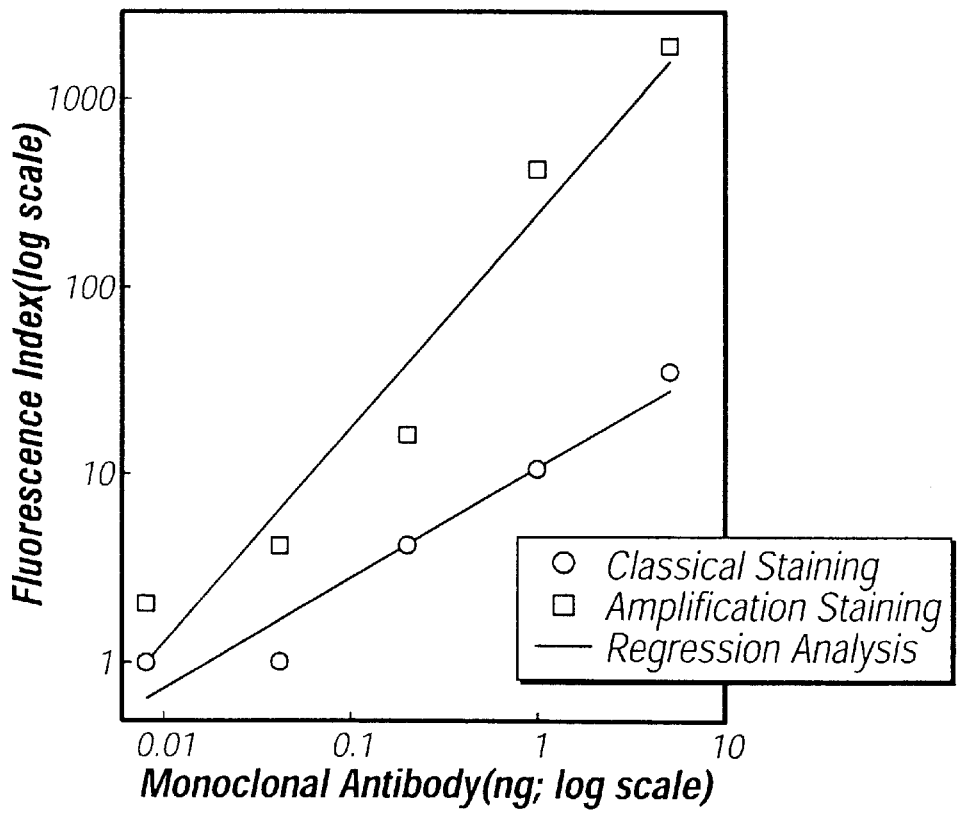
FIG. 2 shows the results of flow cytometric assays of cells expressing MHC class I molecule which have been exposed to increasing concentrations of anti-MHC class I antibody and have been stained by either standard staining methods or by tyramide coating. The y axis represents the Fluorescence Index in which an index of 1 indicates no specific staining. The x axis represents the increase in concentration of the monoclonal antibody.
Figure 3:
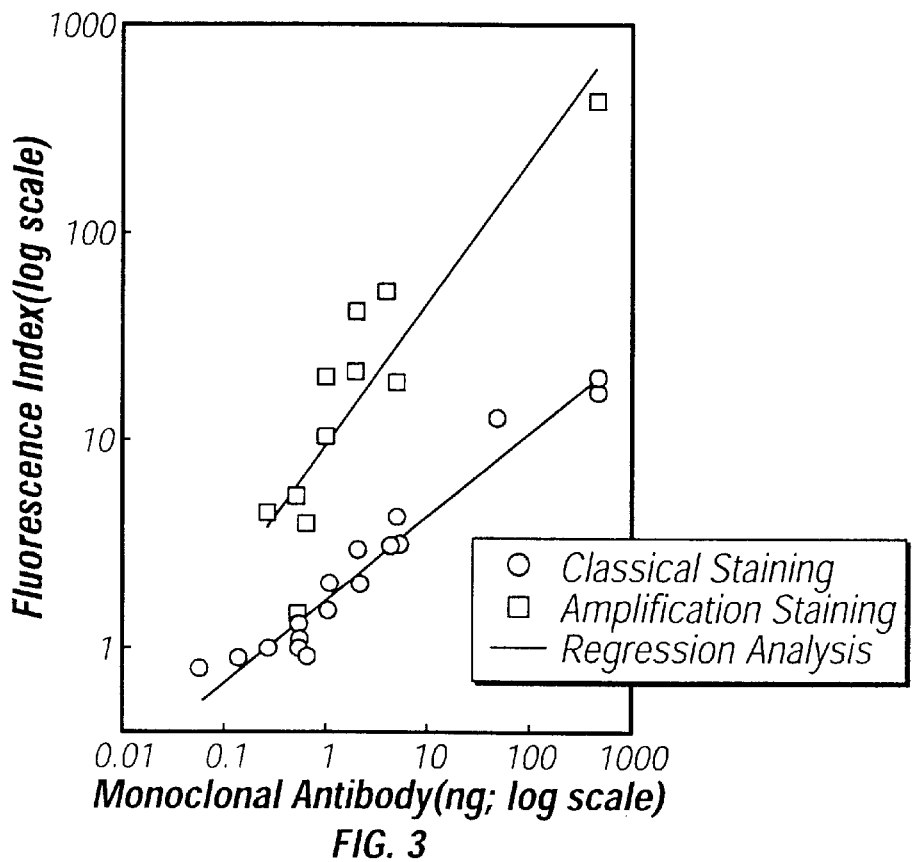
FIG. 3 shows the results of flow cytometric assays of cells expressing CD3 which have been exposed to increasing concentrations of anti-Fas ligand antibody (beginning with sub-optimal conditions) and have been stained by either standard staining methods or by tyramide coating. The y axis represents the Fluorescence Index in which an index of 1 indicates no specific staining. The x axis represents the increase in concentration of the monoclonal antibody.

The method of tyramide coating live cells for flow cytometric analysis represents a new method for detecting and/or quantitating cellular analytes. The present invention offers a method which allows for better detection of cell surface molecules and moreover allows for detection of cellular analytes by flow cytometry by using lower concentrations of antibodies (see FIGS. 2 and 3), antibodies of lower affinity and will allow the detection and analysis of molecules previously incapable of being detected by less sensitive flow cytometric methods. Hence, the present invention offers a more sensitive method for flow cytometric analysis of cellular analytes in samples of live cells.

Standard Flow Cytometry

Flow cytometry permits sensitive detection and rapid quantification of some features of single cells, such as relative size complexity, and endogenous fluorescence, as well as the quantitative analysis of any cellular compound that can be labeled with a fluorochrome. General technical basis and a review of applications of flow cytometry can be found in Melamed, M. R. et al., "Flow Cytometry and Cell Sorting",$2^{nd}$ed. Wiley-Liss, New York (1990) which is incorporated herein by reference in its entirety including any drawings. One of the main achievements of flow cytometry is the rapid quantification of analytes on a large number of, single particles or cells.

The flow cytometer is an instrument that analyses cells one at a time by producing a stream of fluid containing the cells. This stream is focused so that it passes through a laser beam of a defined wavelength. Generally, the fluorochromes selected for use as detectable markers are selected based on the ability of the fluorochrome to fluoresce when excited by light with the wavelength used by the laser. When the fluorochrome is excited by the laser beam, it emits light which is then assessed by the photomultiplier tubes of the flow cytometer. This technique is capable of analyzing 10,000 cells within 1 to 2 minutes. Furthermore, as discussed above, currently available flow cytometers have filters to detect the emittance from various fluorochromes which fluoresce at different wavelengths, and allow for up to four different fluorochromes to be used as detectable markers which means currently at least up to 4 different molecules may be detected simultaneously.

One limitation of standard or standard flow cytometric analysis has been the sensitivity of the technique. Cells to be assessed by flow cytometry are reacted in the cold with antibodies specific for defined cell surface molecules. The antibodies are generally labeled with a fluorescent molecule, although a second reaction with a molecule which possesses a fluorescent label that can bind bound antibody can also be used as a detectable marker. After labeling the cells with cell surface molecule specific antibodies and after washing the cells to remove any unbound antibodies, the cells are placed into a flow cytometer. Using this method the analyte of interest would have to be represented on the cell surface in multiple copies, or multiple antibodies would have to be prepared for different epitopes of the analyte, in order to detect the amount of fluorescent marker that has bound via antibody to the cell surface antigen.

Although flow cytometry has been used successfully for many different molecules, it is considerably less sensitive than many other procedures for the detection of cell surface molecules. As an example, cells that have been transfected to express the cytotoxic molecule Fas ligand on their surface are capable of being detected by using a cytotoxic assay. However, even though detection of expression of Fas ligand is possible by analysis of the transfected cells capability of killing target cells sensitive to Fas ligand, we were unable to detect the expression of Fas ligand by conventional flow cytometric analysis.

Amplification Staining

Amplification staining has been found to be of importance in the detection of cellular analytes for various immunological and immunogenetic procedures. For methods of immunohistochemistry (analysis of slide fixed tissues or cell samples by fluorescent microscopy) the use of enzyme based amplification staining methods has led to enhanced sensitivity.

The Catalyzed Reporter Deposition (CARD) method described by Bobrow et al "Catalyzed Reporter Deposition, A Novel Method Of Signal Amplification", *Journal of Immunological Methods*, 125: 279–285 (1989) and 137: 103–112 (1991) is an amplification staining method used for both immunohistochemical methods, microplate immunoassays (such as ELISAs) as well as membrane immunoassays. Both the CARD method or the analyte dependent enzyme activation system refer to an enzyme system where an enzyme is coupled to a member of a specific binding pair, the enzyme then catalyzes the formation of an activated conjugate which is deposited wherever a receptor for the activated conjugate is immobilized. This system has led to methods for maximizing the sensitivity of methods aimed at the cellular localization of proteins and nucleic acids, especially in cases where target levels are known or suspected to be low. These methods have evolved to improve the sensitivity of both immunohistochemistry and in situ hybridization techniques.

Tyramide Coating Live Cells for Flow Cytometry

In order to enhance the sensitivity of flow cytometric analysis, we have provided a system of amplified reporter deposition. As described in Example I, the current method preferably employs the use of biotinylated antibodies specific for cell surface molecules, a steptavidin-horseradish peroxidase and the substrate peroxide and a reporter molecule such as tyramide. The enzyme reacts with its' substrate to produce oxygen radicals which interact with the phenolic group of tyramide to create a short lived radical activated phenolic substrate. It is believed that the radical activated phenolic substrate binds with electron rich moieties such as tyrosine and tryptophan present in the proteins found on most cell surfaces. It is for this reason that in a preferred embodiment tyramide may be replaced with a phenolic molecule which can be attached to a binding partner. Tyramide can be readily attached to fluorescein, biotin or rhodamine as described in Anton H. N. et al., "Rapid Synthesis of Biotin-, digoxigenin-, Trinitrophenyl-, and Fluorochrome-labeled Tyramides and Their Application for In Situ Hybridization using CARD Amplification", *The Journal of Histochemistry and Cytochemistry*, Vol. 46(6): 771–777, (1998), which is herein incorporated by reference in its entirety including any drawings.

Figure 1A:
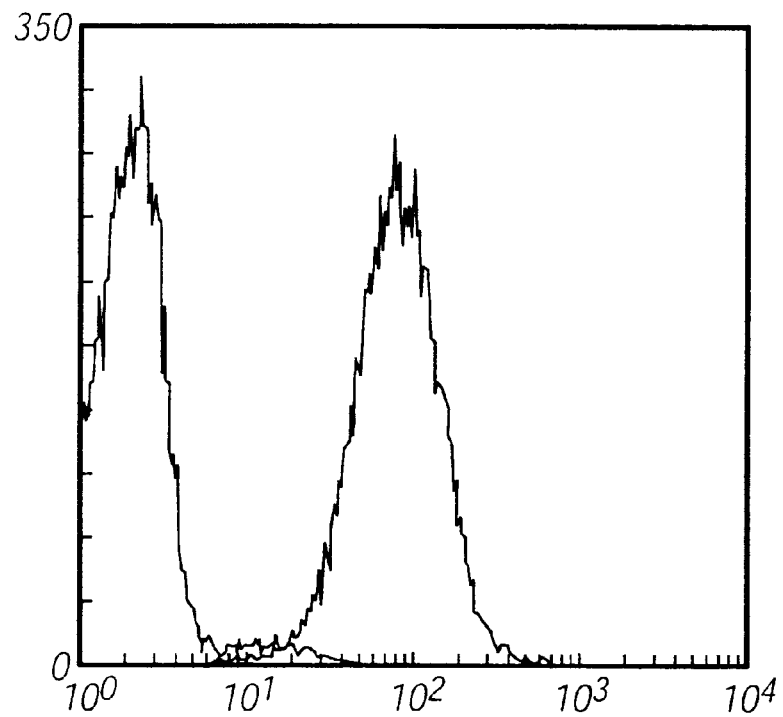
FIGS. 1a and 1b shows the comparison of flow cytometric detection of human class I MHC molecule on Jurkat cells that have been prepared for flow cytometric analysis by (FIG. 1a) standard staining methods or (FIG. 1b) by tyramide coating.
Figure 1B:
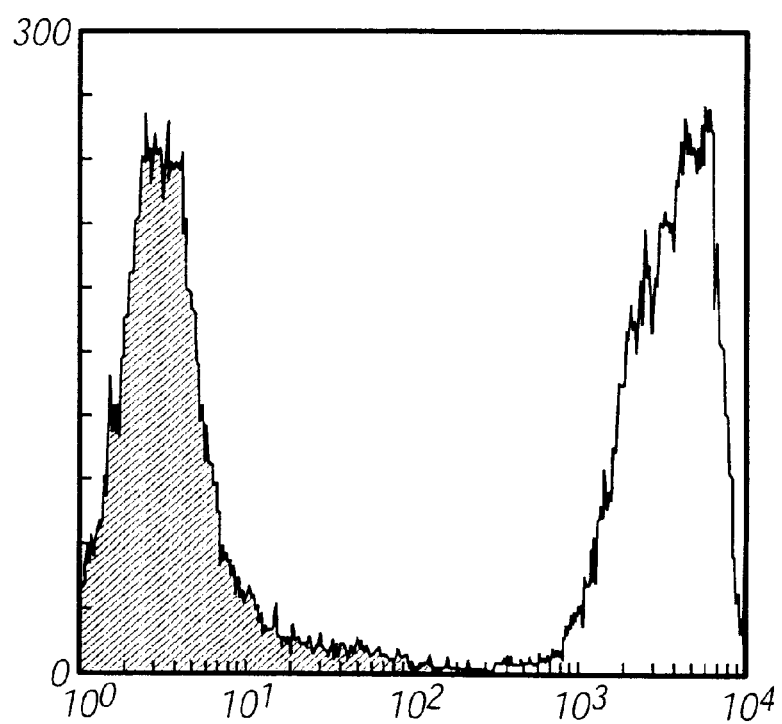

We have investigated the potential of enzymatic amplification to enhance signals in flow cytometry. KFL9 and K562 cells labeled with Anti-Fas ligand monoclonal antibody when incubated with the enzymatic incubation steps as described in Example I, step 3, produced a 4 to 5 fold increase in fluorescent signal when compared to cells incubated without the enzymatic amplification step. The enhancement in the signal indicates that the use of this technology will allow more sensitivity in the detection of cell surface molecules which will be advantageous for both diagnostic and research applications. We have used amplification staining with flow cytometry to enhance the specific fluorescence signal up to 61 fold greater than in standard flow cytometric staining in assessing the expression of cell surface molecules (FIG. 1).

Figure 5A:
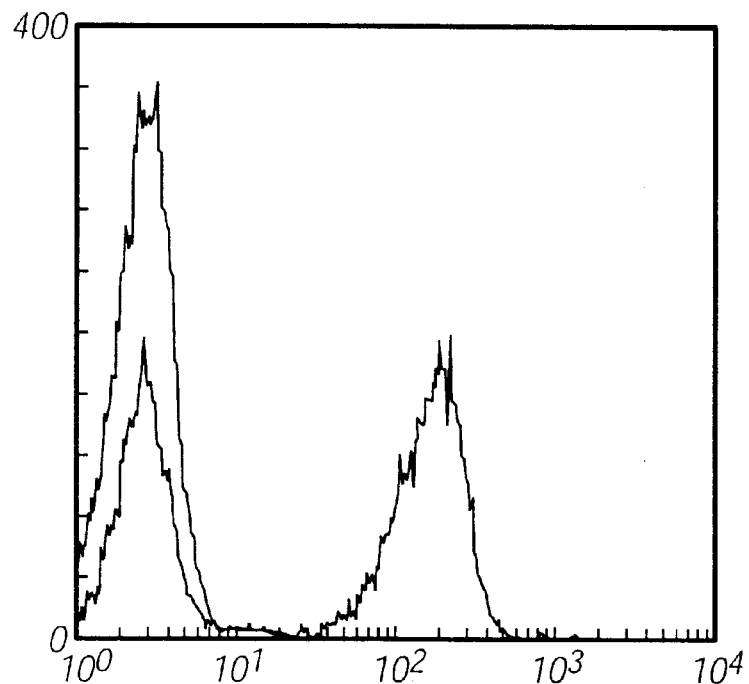
FIG. 5a shows the results of standard flow cytometric detection of the analyte CD5 in a population of CD5 positive and CD5 negative cells.
Figure 5B:
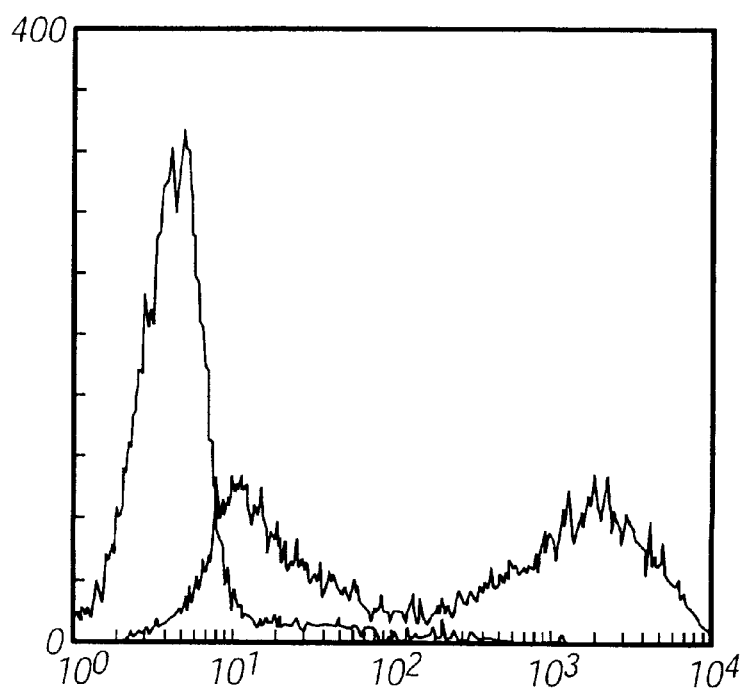
FIG. 5b shows the results of flow cytometric detection of the analyte CD5 in a tyramide coated population of CD5 positive and CD5 negative cells, where the tyramide coating procedure was performed incorporating methods to eliminate bystander staining.
Figure 5C:
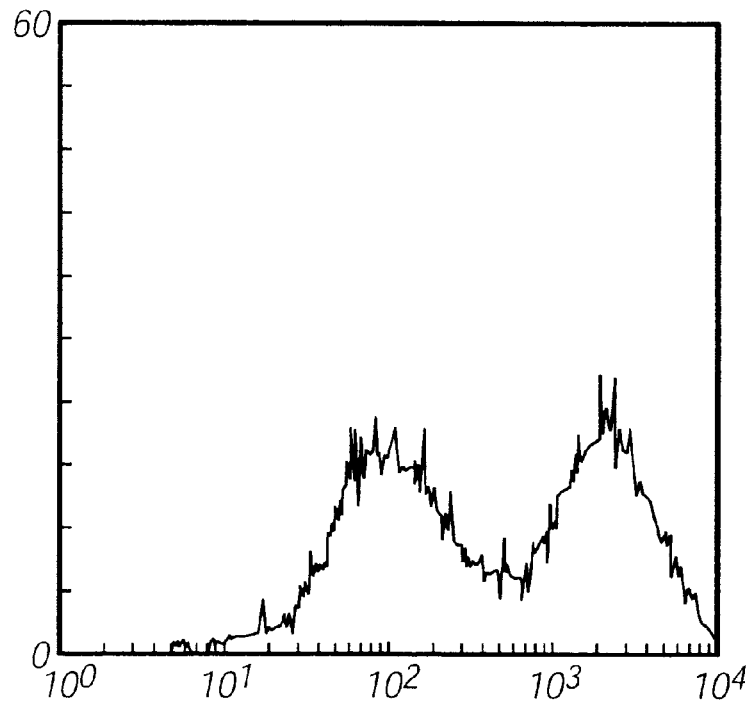
FIG. 5c shows the results of flow cytometric detection of the analyte CD5 in a tyramide coated population of CD5 positive and CD5 negative cells, without incorporating methods to eliminate bystander staining.

A phenomenon of an aspect of amplification staining has been termed "bystander staining". Bystander staining refers to the staining of negative cells in test tubes that include both analyte positive and negative cells. When analyte negative cells are amplification stained for flow cytometry using control antibodies which should not bind the cell there is no detectable staining of the cells other than background staining which is commensurate with that found in standard staining procedures. However, if there are both negative and positive analyte cells in the same test tube, the amplification staining procedure may stain both the positive and negative cells. The elimination of bystander staining occurs in the amplification step of the method (step 4 of Example 1). By resuspending the cells in a low volume 25 to 100 microliters of Ficoll/Hypaque, pH 8.5 with or without the addition of exogenous protein such as milk protein the bystander staining effect is reduced and almost eliminated (FIG. 5). This step strengthens the overall specificity of the method, however it is still possible to differentiate analyte positive cells from analyte negative cells based on their respective fluorescence without eliminating bystander staining.

Figure 6A:
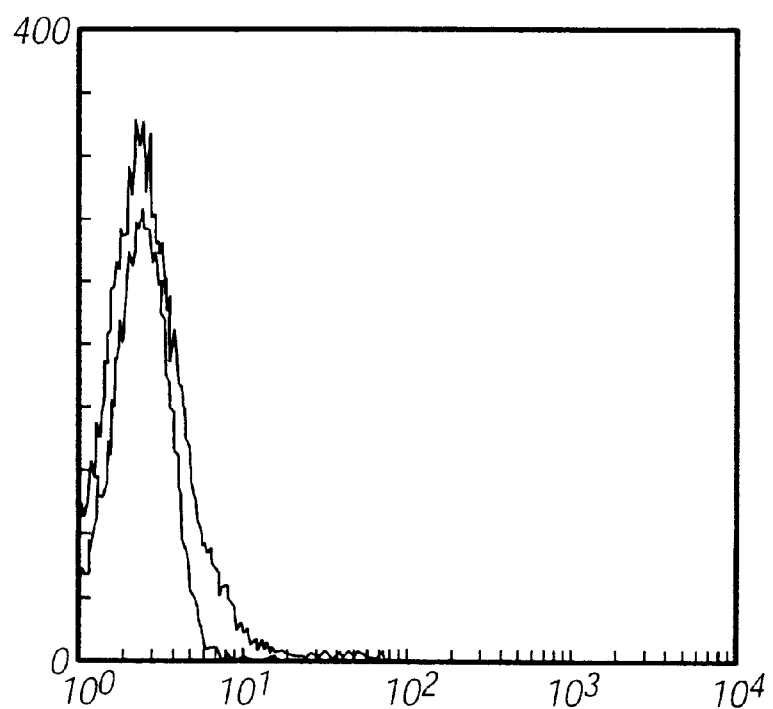
FIG. 6a shows the results of tyramide coating the cells for flow cytometry. One peak in the histogram represents the tyramide coating a control sample of cells, while the other peak represents cells which have been tyramide coated to detect Fas ligand using a specific binding partner (monoclonal antibody specific for Fas ligand.
Figure 6B:
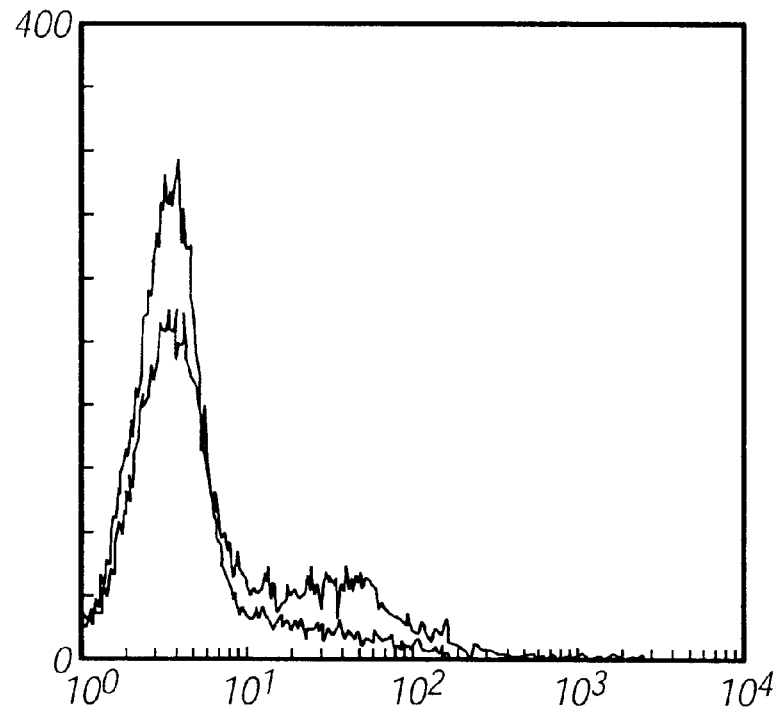
FIG. 6b shows the results of a serial amplification tyramide coating procedure to detect the presence of Fas ligand.

Cell surface analytes can be present on a cell surfaces in amounts which are not easily detectable by current methods. For example, peripheral blood mononuclear cells treated for 3 days in culture medium with phytohemagglutinin and interleukin 2 have stimulated FAS ligand activity which can be measured in a cytotoxicity assay and is indicative of the presence of FAS ligand. Cells which have been exposed to phytohemaggluting an interleukin 2 in such a manner are positive for FAS ligand activity in a cytotoxicity assay. However detecting FAS ligand on these cells by flow cytometric analysis is inconclusive for the presence of the cell surface molecule using standard flow cytometric means (FIG. 6a). Surprisingly, FAS ligand can be detected by tyramide coating the cell surface using serial amplification. FIG. 6b, shows the detection of FAS ligand on cells which were positive when analyze by cytotoxic activity but were inconclusive for FAS ligand when analyzed by standard flow cytometric methods. These cells when analyzed by flow cytometry using serial amplification methods as described herein are positive for the presence of the cell surface molecule FAS ligand.

Figure 7:
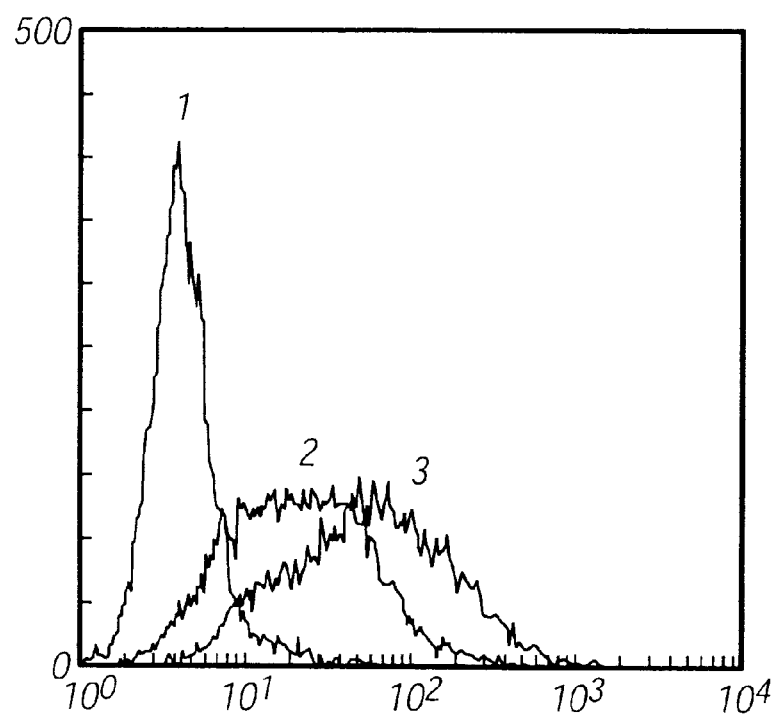
FIG. 7 shows three histogram peaks. The tallest peak (histogram 1) represents K562 cells which have been tyramide coated by single cycle serial amplification to determine the presence of Fas ligand. Histogram 2 represents the results of tyramide coating by single cycle serial amplification to determine the presence of Fas ligand on the surface of KFL9 cells which express the ligand. Histogram 3 represents the result of tyramide coating by 2 cycle serial amplification to determine the presence of Fas ligand on the surface of KFL9 cells which express the ligand.

Furthermore, we have shown that additional cycles of serial amplification for tyramide coating results in improved detection of cell surface analytes. K562 cells do not normally express Fas ligand, as shown in FIG. 7. When K562 cells are analyzed for the presence of FAs ligand by tyramide coating using amplification staining and flow cytometry the results are negative (FIG. 7). KFL9 cells express Fas ligand on their surface. FIG. 7 illustrates the improved staining which results from additional cycles of serial amplification staining.

Those in the art will appreciate that the method of the invention can be used for a variety of flow cytometric analysis methods for analyte detection in live cell samples. Also, those in the art would recognize that more than one fluorochrome may be used depending on the quality of the flow cytometer used for analysis. In addition, with the inventive teachings described herein, incorporation of more than one fluorochrome onto cells assayed for more than one cell surface molecule could provide a method for the rapid detection of more than one analyte of interest in a sample of live cells.

EXAMPLES

The following examples serve to illustrate the method for amplification staining live cells for flow cytometry of the invention. These examples are in no way intended to limit the scope of the invention.

Example I
Tyramide Coating Live Cells for Flow Cytometric Analysis
1. A sample of live cells expressing or presumed to be expressing a cell surface analyte of interest are added to a test tube.
2. To this sample, antibody (or antibody conjugate) specific for the analyte is added in a physiological buffer, such as phosphate buffered isotonic saline with 0.005% azide and 1% bovine serum albumin, at room temperature. The cells are washed once in with the same medium without antibody.
3. Add a substance with enzymatic activity (streptavidin-horseradish peroxidase) that will bind to antibody or antibody conjugate. Cells are incubated in a physiological buffer (as above) at room temperature. The cells are washed in phosphate buffered isotonic saline.
4. Tyramide-biotin molecules and peroxide are added to the cells in a solution of Ficoll/Hypaque, pH 8.5 in a small or low volume 25 to 100 microliters in the presence or absence of exogenous proteins (such as milk protein). Cells are incubated at room temperature in a physiological buffer that does not contain azide. The cells are washed with phosphate buffered saline and once with phosphate buffered saline with added sodium azide and bovine serum albumin.
5. Streptavidin-fluorochrome molecules are added to the cells in phosphate buffered saline with added sodium azide and bovine serum albumin. The cells are washed and the analyzed by flow cytometry (A washing step may be included between each of steps 1, 2, and 3. Steps 2 and 3 may be combined with the use of an antibody conjugated to an enzyme as shown below).

Figure 4A:
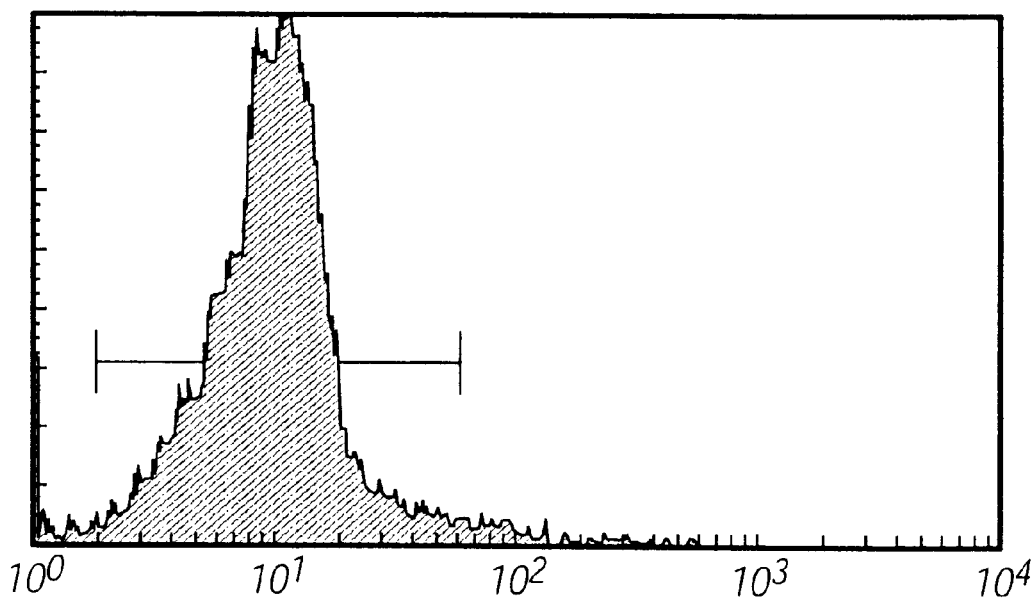
FIG. 4a represents the results obtained using control antibody molecules conjugated to horseradish peroxidase.
Figure 4B:
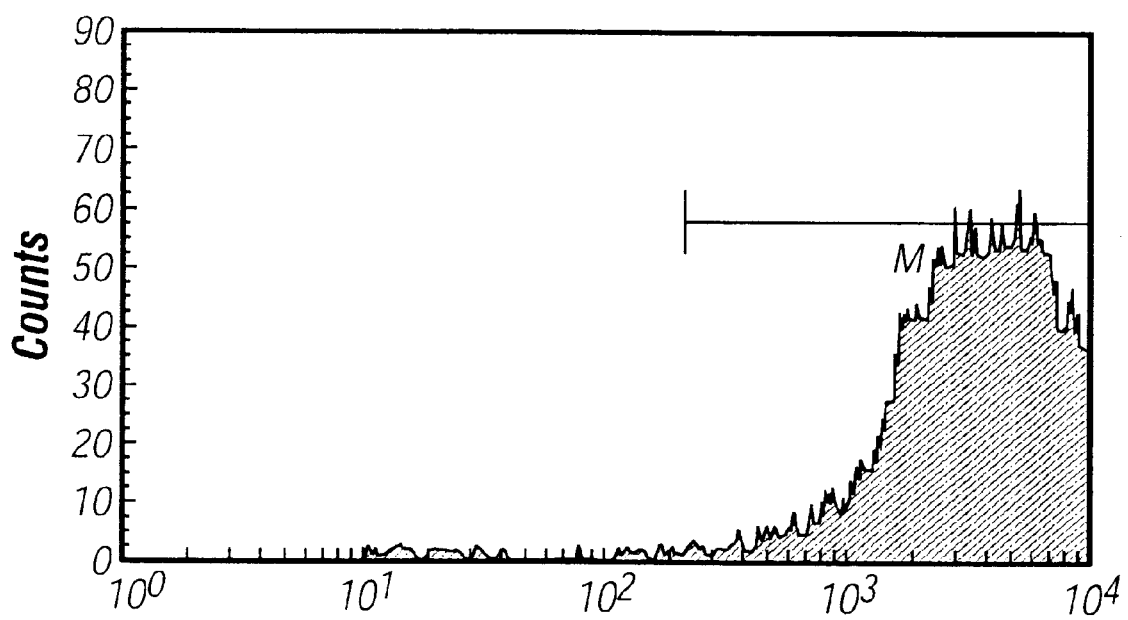
FIG. 4b represents the results obtained using antibody molecules directly conjugated to horseradish peroxidase specific for CD45.

Example 2
Detection of CD45 with Conjugated Monoclonal Antibody
1. A sample of Jurkat cells are added to two test tubes, a control tube and experimental tube.
2. To the control sample control antibody conjugated with horseradish peroxidase is added and to the experimental sample antibody specific for CD45 conjugated with horseradish peroxidase. Both samples are suspended in a physiological buffer, such as isotonic saline with 0.005% sodium azide, at room temperature.
3. After the cells are washed, tyramide-biotin molecules and hydrogen peroxide are added to the samples in a solution of Ficoll/Hypaque, pH 8.5 in a small or low volume (25 to 100 microliters) in the presence or absence of exogenous proteins (such as milk protein). Cells are incubated at room temperature in a physiological buffer that does not contain azide.
4. After cells are washed, streptavidin-fluorochrome molecules are added to the cells, the samples are washed and the analyzed by flow cytometry The results demonstrate that antibodies directly conjugated to horseradish peroxidase work well in the amplification procedure. (see FIG. 4)

Example 3
Elimination of Bystander Staining
1. A sample of Jurkat (CD5 positive) and K562 (CD5 negative) cells of approximately equal numbers is added to a test tube.
2. To this sample, antibody (or antibody conjugate) specific for the analyte, CD5, is added in a physiological buffer, such as phosphate buffered isotonic saline with 0.005% azide and 1% bovine serum albumin, at room temperature. The cells are washed once in with the same medium without antibody.
3. Add a substance with enzymatic activity (streptavidin-horseradish peroxidase) that will bind to antibody or antibody conjugate. Cells are incubated in a physiological buffer (as above) at room temperature. The cells are washed in phosphate buffered isotonic saline.
4. Tyramide-biotin molecules and peroxide are added to the cells in a solution of Ficoll/Hypaque, pH 8.5 in a small or low volume 25 to 100 microliters in the presence or absence of exogenous proteins (such as milk protein). Cells are incubated at room temperature in a physiological buffer that does not contain azide. The cells are washed with phosphate buffered saline and once with phosphate buffered saline with added sodium azide and bovine serum albumin.
5. Streptavidin-fluorochrome molecules are added to the cells in phosphate buffered saline with added sodium azide and bovine serum albumin. The cells are washed and the analyzed by flow cytometry.

Samples contained CD5 positive and CD5 negative populations of approximately equal numbers.

Example 4
Amplification Staining of Live Cells for Flow Cytometry

1. Place half a million cells in 12×75 mm squared round bottom tubes.
2. Wash the cells once with phosphate buffered isotonic saline (pH 7.3) with 1% bovine serum albumin and 0.005% sodium azide (referred to as staining buffer).
3. Add to the cells biotinylated antibody (0.5–1 microgram) specific for analyte in 50 microliters of staining buffer and incubate for 10 minutes at room temperature in the dark.
4. Wash the cells one or two times with staining buffer.
5. Add to the cells streptavidin conjugated with horseradish peroxidase in 50 microliters of staining buffer and incubate for 10 minutes at room temperature in the dark.
6. Wash the cells one time with phosphate buffered isotonic saline, pH 7.3.
7. Wash the cells one time with phosphate buffered isotonic saline, pH 7.3 containing 0.01% hydrogen peroxide.
8. Add to the cells biotinylated tyramide (1–1.5 mg/ml) in 50 microliters of Histopaque (Sigma brand name of Ficoll/Hypaque, density 1.077) containing 0.01% hydrogen peroxide. Incubate the suspension for 10 minutes at room temperature in the dark.
9. Wash the cells one time with phosphate buffered isotonic saline, pH 7.3 and one time with staining buffer.
10. Add to the cells 0.5 microgram streptavidin conjugated with a fluorochrome such as phycoerythrin-CY5 in 50 microliters of staining buffer. Incubate for 10 minutes at room temperature in the dark.
11. Wash the cells one or two times with staining buffer and resuspend in 0.5 milliliters of staining buffer.
12. Analyze the cells on a FACScan II flow cytometer with the following photomultiplier tube voltage settings: Forward scatter channel, E00; side scatter channel, 507; FL1, 620; FL2, 603; and FL3, 650. The amplification gain settings are: forward scatter channel, 1.5; and side scatter channel, 1.0.

Example 5
Serial Amplification Staining Method

1. Place half a million cells in 12×75 mm squared round bottom tubes.
2. Wash the cells once with phosphate buffered isotonic saline (pH 7.3) with 1% bovine serum albumin and 0.005% sodium azide (referred to as staining buffer).
3. Add to the cells biotinylated antibody (0.5–1 microgram) specific for Fas ligand analyte in 50 microliters of staining buffer and incubate for 10 minutes at room temperature in the dark.
4. Wash the cells one or two times with staining buffer.
5. Add to the cells streptavidin conjugated with horseradish peroxidase in 50 microliters of staining buffer and incubate for 10 minutes at room temperature in the dark.
6. Wash the cells one time with phosphate buffered isotonic saline, pH 7.3.
7. Wash the cells one time with phosphate buffered isotonic saline, pH 7.3 containing 0.01% hydrogen peroxide.
8. Add to the cells biotinylated tyramide (1–1.5 mg/ml) in 50 microliters of Histopaque (Sigma brand name of Ficoll/Hypaque, density 1.077) containing 0.01% hydrogen peroxide. Incubate the suspension for 10 minutes at room temperature in the dark.
9. Wash the cells one time with phosphate buffered isotonic saline, pH 7.3 and one time with staining buffer.
10. Repeat steps 5–9 at least once.
11. Add to the cells 0.5 microgram streptavidin conjugated with a fluorochrome such as phycoerythrin-CY5 in 50 microliters of staining buffer. Incubate for 10 minutes at room temperature in the dark.
12. Wash the cells one or two times with staining buffer and resuspend in 0.5 milliliters of staining buffer.
13. Analyze the cells on a FACScan II flow cytometer with the following photomultiplier tube voltage settings: Forward scatter channel, E00; side scatter channel, 507; FL1, 620; FL2, 603; and FL3, 650. The amplification gain settings are: forward scatter channel, 1.5; and side scatter channel, 1.0.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods, substituents (such as buffers, fluorochromes, enzymes and substrates), and target materials described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, those skilled in the art will readily recognize that the present methods can incorporate a variety of different cell types, physiological buffers, enzyme-substrate systems, and different target materials. Thus, such additional embodiments are within the scope of the present invention and the following claims.

The invention illustratively described herein suitably may be practiced in the absence of any element or elements, limitation or limitations, which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Thus, additional embodiments are within the scope of the invention and within the following claims.

What I claim is:

1. A method of detecting the presence of an analyte on a surface of one or more cells by flow cytometry, the method comprising:
    a) specifically coating one or more unfixed cells comprising a surface analyte with tyramide by catalyzing the deposition of tyramide on the surface of said cells, wherein said coating of one or more cells is performed under conditions that inhibit bystander staining;
    b) contacting said one or more cells coated with tyramide with a detectable label that directly or indirectly binds to tyramide; and
    c) detecting a signal from said label using a flow cytometric device that is at least 10-fold greater than a signal obtainable by standard flow cytometry methods, wherein said signal indicates the presence of said analyte on the surface of said cells.

2. A method of detecting the presence of an analyte on a surface of one or more cells by flow cytometry, the method comprising:
    a) specifically coating one or more unfixed cells comprising a surface analyte with tyramide conjugated to a detectable label by catalyzing the deposition of tyramide conjugated to said label on the surface of said cells wherein said coating of one or more cells is performed under conditions that inhibit bystander staining;
    b) detecting a signal from said label using a flow cytometric device that is at least 10-fold greater than a signal obtainable by standard flow cytometry methods, wherein said signal indicates the presence of said analyte on the surface of said cells.

3. The method of claim 1 or 2 wherein said signal is at least 40-fold greater than a signal obtainable by standard flow cytometry methods.

4. The method of claim 1 or 2 wherein said signal is at least 50-fold greater than a signal obtainable by standard flow cytometry methods.

5. The method of claim 1 or 2, wherein said conditions that inhibit bystander staining comprise performing said coating step in the presence of an aqueous solution comprising a neutral, branched hydrophilic sucrose polymer having an average molecular weight of 400,000 and sodium diatrizoate.

6. The method of claim 1 or 2, wherein said conditions that inhibit bystander staining comprise performing said coating step at a pH of about 8.4.

7. The method of claim 1 or 2, wherein said one or more cells are one or more live cells.

8. The method of claim 1, wherein said coating step comprises contacting said one or more cells with a first binding partner specific for said surface analyte, wherein said first binding partner comprises an enzyme.

9. The method of claim 7, wherein said coating step comprises contacting the live cells with a first binding partner specific for an analyte of interest, and a second binding partner specific for said first binding partner, wherein said second binding partner comprises an enzyme.

10. The method of claim 2, wherein said coating step comprises contacting said one or more cells with a first binding partner specific for said surface analyte, wherein said first binding partner comprises an enzyme.

11. The method of claim 2, wherein said coating step comprises contacting the live cells with a first binding partner specific for an analyte of interest, and a second binding partner specific for said first binding partner, wherein said second binding partner comprises an enzyme.

12. The method of any one of claim 8, 9, 10, or 11 wherein said enzyme is selected from the group consisting of hydrolysases, peroxidases, oxidases, esterases, glycosidases and phosphatases.

13. The method of any one of claim 8, 9, 10, or 11 wherein said enzyme is horseradish peroxidase.

14. The method of claim 9 or 11 wherein said second binding partner is a streptavidin-enzyme conjugate.

15. The method of claim 14, wherein said streptavidin-enzyme conjugate is selected from the group consisting of streptavidin-peroxidase, streptavidin-hydrolase, streptavidin-oxidase, streptavidin-gycosidase and streptavidin-phosphatase.

16. The method of claim 14, wherein said streptavidin-enzyme conjugate is streptavidin-horseradish peroxidase.

17. The method of any one of claim 8, 9, 10, or 11 wherein said coating step comprises contacting the cells with a substrate for said enzyme.

18. The method of claim 17, wherein said substrate is peroxide.

19. The method of claim 18, wherein said peroxide is present at a concentration of about 0.01%.

20. The method of claim 1 or 2, wherein said detectable label comprises a fluorochrome.

21. The method of claim 1 or 2, wherein said detectable label is a detectable phenol conjugated molecule.

22. The method of claim 1 or 2, wherein said tyramide is conjugated to biotin.

23. The method of claim 1 or 2, wherein said one or more cells are one or more mammalian cells.

24. The method of claim 23, wherein said one or more mammalian cells are selected from the group consisting of basal cells, epithelial cells, erythrocytes, platelets, lymphocytes, T-cells, B-cells, natural killer cells, granulocytes, monocytes, mast cells, Jurkat cells, neurocytes, neuroblasts, cytomegalic cells, dendritic cells, macrophages, blastomeres, endothelial cells, HeLa cells, tumor cells, interstitial cells, Kupffer cells, Langerhans' cells, Langhans cells, littoral cells, tissue cells, adipose cells, CHO cells, KFL9, and K562 cells.

25. The method of claim 1 or 2, wherein said cell surface analyte is selected from the group consisting of Fas ligand, CD1 through CD166, MHC class I, MHC class II, tumor antigens, virus antigens, cell receptors for IgG, and IgE, cell receptors for complement components C3a, C5a, CR1 and CR3, T-Cell or B-Cell B-Cell receptor molecules, viral antigens, tumor antigens, histocompatibility antigens, and differentiation antigens.

26. The method of claim 1 or 2, wherein said cell surface analyte is not a natural component of said one or more cells.

27. The method of claim 1 or 2, wherein said cell surface analyte cannot be detected by standard flow cytometry methods.

28. The method of claim 1 or 2, wherein said one or more cells are obtained from a patient.

29. The method of claim 28, wherein said signal is correlated to a diagnosis of a disease in said patient.

30. A method of detecting the presence of an analyte on a surface of one or more cells by flow cytometry, the method comprising:

a) contacting said one or more unfixed cells with a first binding partner specific for a cell surface molecule, a second binding partner with enzymatic activity, said second binding partner specific for said first binding partner, a third binding partner specific for a second cell surface molecule, a fourth binding partner with enzymatic activity, said fourth binding partner specific for said third binding partner, a substrate for said enzymatic activity of the second and the fourth binding partners, and a detectable label comprising tyramide, wherein said second and fourth binding partners react with said substrate to specifically coat said one or more cells comprising said cell surface molecule with said tyramide under conditions that inhibit bystander staining; and b) detecting a signal from said label using a flow cytometric device that is at least 10-fold greater than a signal obtainable by standard flow cytometry methods, wherein said signal indicates the presence of said analyte on the surface of said cells.

* * * * *